United States Patent
Sagawa et al.

(10) Patent No.: US 6,452,026 B1
(45) Date of Patent: Sep. 17, 2002

(54) PROCESS FOR PRODUCING OPTICALLY ACTIVE THREO-3-AMINO-1,2-EPOXY COMPOUNDS

(75) Inventors: Yukihiro Sagawa, Saitama; Jouji Sekine, Tokyo; Hisao Sato, Saitama, all of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/997,875

(22) Filed: Nov. 30, 2001

Related U.S. Application Data

(62) Division of application No. 09/600,215, filed on Jul. 12, 2000, now Pat. No. 6,376,685.

Foreign Application Priority Data (30)

Jan. 28, 1998 (JP) .............................................. 10-29059

(51) Int. Cl.$^7$ ............................................ C07D 301/02
(52) U.S. Cl. ...................................................... 549/518
(58) Field of Search ............................................ 549/518

(56) References Cited

U.S. PATENT DOCUMENTS

| | | | |
|---|---|---|---|
| 5,481,011 A | 1/1996 | Chen et al. | 549/514 |
| 5,488,118 A | 1/1996 | Koshigoe et al. | 549/518 |
| 5,516,784 A | 5/1996 | Bennett et al. | 514/311 |
| 5,847,169 A | 12/1998 | Nummy et al. | 549/521 |

FOREIGN PATENT DOCUMENTS

| | | |
|---|---|---|
| EP | 0 430 096 | 6/1991 |
| JP | 3-251577 | 11/1991 |
| JP | 7-215955 | 8/1995 |
| JP | 8-225557 | 9/1996 |

*Primary Examiner*—Joseph K. McKane
*Assistant Examiner*—Joseph Murray
(74) *Attorney, Agent, or Firm*—Nields & Lemack

(57) ABSTRACT

Highly pure optically active threo-3-amino-1,2-epoxy compounds appropriate for materials for manufacturing drugs and a process for producing the same on an industrial scale. An optically active threo-3-amino-1,2-diol derivative is subjected in an organic solvent in the presence of a base to alkylsufonylation or arylsulfonylation to thereby give the corresponding optically active threo-3-amino-2-hydroxy-1-sulfonyloxy compound. Next, the resultant product is subjected to epoxidation in the presence of a base to give the corresponding optically active threo-3-amino-1,2-epoxy compound. The thus obtained epoxy compound is purified by using an organic solvent and water, thus giving a highly pure epoxy compound.

9 Claims, No Drawings

PROCESS FOR PRODUCING OPTICALLY ACTIVE THREO-3-AMINO-1,2-EPOXY COMPOUNDS

This application is a Divisional of Ser. No. 09/600,215 filed on Jul. 12, 2000 now U.S. Pat. No. 6,376,685.

TECHNICAL FIELD

The optically active threo-3-amino-1,2-epoxy compounds in the present invention are used as a synthetic material for intermediates of drugs. For example, they are used for the intermediates of HIV protease inhibitor (JP Laid-Open No.257554/1992) or an enzyme inhibitor. The present invention is expected to be an industrial process for producing the optically active threo-3-amino-1,2-epoxy compounds.

BACKGROUND ART

The known processes for producing the optically active threo-3-amino-1,2-epoxy compounds represented by the formula (3) are as follows:

① the process, wherein a 3-substituted-3-amino-2-oxo-1-halogenopropane is subject to the reduction at the 2-ketone site to derive the halohydrine compound, and then the halohydrine compound is subject to the dehydrohalogenation with a base to obtain the epoxy compound (U.S. Pat. No. 5,559,256, EP-580402, J. Med. Chem., 37, 1785(1994));

② the process, wherein a 3-substituted-3-aminoaldedyde derivative is reacted with a diholomethane or a disulfonium ylide to obtain the epoxy compound(WO93/23388, J. Med. Chem., 35, 2525(1992), Tetrahedron Lett., 30,5425(1989), J. Org. Chem., 50,4615(1985));

③ the process, wherein a 3-substituted-3-amino-1-propene derivative is reacted with a peroxy acid to obtain the epoxy compound(WO96/04277, EP-532466, CA-2075666, JP Laid-Open No.257520/1992, J. Org. Chem., 52,1487(1987));

④ the process, wherein a 3-amino-1,2-diol derivative is reacted with p-toluene sulfonyl chloride to give a 3-amino-2-hydroxytoluene sulfonate derivative in pyridine, and then the sulfonate derivative is reacted with potassium carbonate or sodium hydride to obtain the epoxy compound(WO97/42180, U.S. Pat. No. 5,516, 784).

However, these processes have their respective drawbacks in the industrial manufacturing, as described below.

In the process ①, since the erythro configuration of a halohydrine derivative is produced preferentially because of reductive selectivity when the 2-ketone group of the 3-substituted-3-amino-2-oxo-1-halogenopropane is reduced to an alcohol group, the threo configuration of the halohydrine derivative, which is unpreferentially produced by the reductive reaction, must be used in order to obtain the optically active threo-3-amino-1,2-epoxy compound.

In the process ②, a ratio of threo- and erythro-epoxy compounds varies depending on the reaction condition or the sort of a 3-substituted group in the reaction in which the 3-substituted-3-aminoaldedyde derivative is reacted with a diholomethane or a disulfonium ylide. Furthermore, 3-substituted-3-aminoaldedyde derivative is defectively liable to a racemization because it is put into a strongly basic reaction system.

For the process ③, which utilizes the 3-substituted-3-amino-1-propene derivative as the reaction material, it is decisively important how the amino derivative or its equivalent can be produced in an industrially reasonable cost. It can be produced from the aminoaldehyde compound through the Wittig Reaction or the Peterson Reaction, but the Wittig Reaction brings troublesomely about racemization and the Peterson Reaction requires a reaction temperature of −65° C. or lower in order to produce the key intermediate, 2-hydroxy-1-trialkylsilyl compound. Furthermore, the epoxydation reaction requires a strict caution in the industrial practice due to peroxy acid used.

With respect to the process ④, it is inconvenient in time and operation for the mass production because a p-toluene sulfonylation is carried out at a relatively low temperature for a long time and, after completion of the reaction, it requires many repetitions of extracting and washing to remove pyridine used for the solvent besides the base and the concentration steps.

Any of ①–④ has never isolated highly pure optically active threo-3-amino-1,2-epoxy compound.

It is desired to improve the processe of producing the threo configuration of an optically active 3-amino-1,2-epoxy compound in order to obtain the threo compound having a purity enough to use for a drug material in an industrial scale because the known processes are not satisfied necessarely.

DISCLOSURE OF THE INVENTION

The present inventors made a diligent study to solve the above problem and, as a result, have found that a highly pure optically active threo-3-amino-1,2-epoxy compound can be industrially produced, either by epoxydating a sulfonylated product obtained by sulfonylation, without isolating it from the organic phase, under the presence of a base, or by depositing selectively the sulfonylated product from the sulfonylation reaction solution and then epoxydating, and thereafter purifying with aliphatic hydrocarbon solvents or/and water.

Namely, the present invention relates to the following term 1 to 34:

1. A process for producing an optically active threo-3-amino-1,2-epoxy compound represented by the formula (3),

(where $R_1$ is a C3–C12 hydrocarbon residual group; $R_2$ is an amino group or a protected amino group; *2 is, if *3 is S in configuration, R in configuration and, if *3 is R in configuration, S in configuration), which comprises reacting an optically active threo-3-amino-1,2-diol derivative represented by the formula (1)

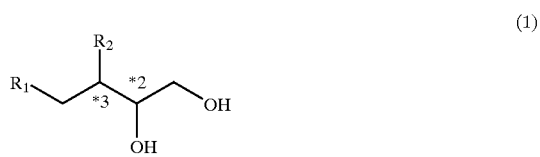

(where $R_1$, $R_2$, *2 and *3 show the same meanings as described above)

with an alkylsulfonyl halogenide or an arylsulfonyl halogenide for sulfonylating under the presence of a base in an organic solvent to obtain site-specifically the optically active threo-3-amino-2-hydroxysulfonate derivative represented by the formula(2)

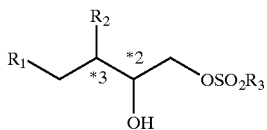

(2)

(where $R_1$, $R_2$, *2 and *3 show the same meaning as described above, and $R_3$ is a C1–C12 hydrocarbon residual group)
and then epoxydating, without isolating from the organic phase, under the presence of a base.

2. A process according to term 1, wherein $R_1$ is a C3–C8 hydrocarbon residual group.
3. A process according to term 1, wherein $R_1$ is a cyclohexyl group or a phenyl group.
4. A process according to any of term 1–3, wherein $R_2$ is an amino group or an amino group protected with an urethane-forming protective group.
5. A process according to term 4, wherein $R_2$ is an amino group protected with an optionally substituted lower alkanoyl group or a lower alkoxycarbonyl group.
6. A process according to term 1, wherein $R_1$ is a cyclohexyl group or a phenyl group, and $R_2$ is a tert-butoxycarbonyl amino group, a benzyloxycarbonyl amino group, or a phthalimino group.
7. A process according to any of term 1–6, wherein $R_3$ is a lower alkyl group or a substituted phenyl group.
8. A process according to any of term 1–7, wherein said organic solvent is an ether type of solvent, an ester type of solvent, an aromatic hydrocarbon type of solvent or a halogenide type of solvent.
9. A process according to term 8, wherein said ether type of solvent is tetrahydrofurane, said ester type of solvent is ethyl acetate, said aromatic hydrocarbon type of solvent is toluene and said halogenide type of solvent is methylene chloride.
10. A process according to term 8, wherein said organic solvent is tetrahydrofurane.
11. A process according to any of term 1–10, wherein said base used for sulfonylating the compound of the formula (1) is a tertiary amine.
12. A process according to term 11, wherein said base is triethylamine.
13. A process according to any of term 1–12, wherein said base used for epoxydating the compound of the formula (2) is an alkali metal alcoholate.
14. A process according to term 13, wherein said base is sodium methylate.
15. A process for producing an optically active threo-3-amino-2-hydroxysulfonate derivative represented by the formula(2)

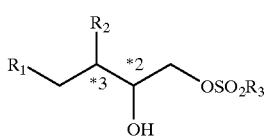

(2)

(where $R_1$, $R_2$, $R_3$, *2 and *3 show the same meanings as described above),
which comprises reacting the optically active threo-3-amino-1,2-diol derivative represented by the formula (1)

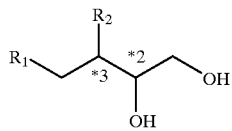

(1)

(where $R_1$, $R_2$, *2 and *3 show the same meanings as described above)
with an alkylsulfonyl halogenide or an arylsulfonyl halogenide under the presence of a base in an organic solvent and then, from the reaction system, depositing the sulfonate derivative of which only the primary hydroxyl group is site-spcifically sulfonylated, so as to prevent the secondary hydroxyl group from being sulfonylated.

16. A process for producing an optically active threo-3-amino-2-hydroxysulfonate derivative, which comprises pouring an ether type of solvent or an aliphatic hydrocarbon type of solvent into the suspension obtained in term 15 so as to increase crystalline deposition.
17. A process according to term 15 or 16, wherein said organic solvent is the mixed solvent of an ester type of solvent with an ether type of solvent, the mixed solvent of an ester type of solvent with an aliphatic hydrocarbon type of solvent, the mixed solvent of an aromatic hydrocarbon type of solvent with an ether type of solvent, or the mixed solvent of an aromatic hydrocarbon type of solvent with an aliphatic hydrocarbon type of solvent.
18. A process according to any of term 15–17, wherein, in said mixed solvent of an ester type of solvent with an ether type of solvent, in said mixed solvent of an ester type of solvent with an aliphatic hydrocarbon type of solvent, in said mixed solvent of an aromatic hydrocarbon type of solvent with an ether type of solvent, or in said mixed solvent of an aromatic hydrocarbon type of solvent with an aliphatic hydrocarbon type of solvent, a volume ratio of the former to the latter is 1:0.1–6.
19. A process according to any of term 15–18, wherein said ester type of solvent is ethyl acetate, said ether type of solvent is isopropylether, said aliphatic hydrocarbon type of solvent is n-heptane and said aromatic hydrocarbon type of solvent is toluene.
20. A process according to term 19, wherein said ester type of solvent is ethyl acetate, said ether type of solvent is isopropylether and, if necessary, n-heptane is used as said aliphatic hydrocarbon type of solvent poured so as to increase crystalline deposition.
21. A process according to term 15, wherein said base is a tertiary amine.
22. A process according to term 21, wherein said base is triethylamine.
23. A process for producing an optically active threo-3-amino-1,2-epoxy compound represented by the formula (3), which comprises epoxydating the optically active threo-3-amino-2-hydroxysulfonate derivative obtained by the process according to any of term 15–22 under the presence of a base in an organic solvent.

24. A process for purifying an optically active threo-3-amino-1,2-epoxy compound represented by the formula (3),

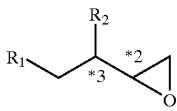
(3)

(where $R_1$ is a C3–C12 hydrocarbon residual group; $R_2$ is an amino group or a protected amino group; *2 is, if *3 is S in configuration, R in configuration and, if *3 is R in configuration, S in configuration),
which comprises reacting the optically active threo-3-amino-1,2-diol derivative represented by the formula (1)

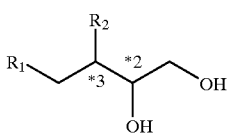
(1)

(where $R_1$, $R_2$, *2 and *3 show the same meanings as described above)
with an alkylsulfonyl halogenide or an arylsulfonyl halogenide for sulfonylating under the presence of a base in an organic solvent to obtain site-specifically the optically active threo-3-amino-2-hydroxysulfonate derivative represented by the formula(2)

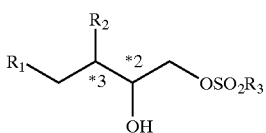
(2)

(where $R_1$, $R_2$, *2 and *3 show the same meaning as described above, and $R_3$ is a C1–C12 hydrocarbon residual group)
and then epoxydating under the presence of a base and thereafter removing selectively a by-product, namely, optically active threo-3-amino-1,2-disulfonate derivative as a depositing crystalline by using an aliphatic hydrocarbon type of solvent and by utilizing difference in solubility between the epoxy compound and the by-product.

25. A process for purifying an optically active threo-3-amino-1,2-epoxy compound according to term 24, wherein the solution obtained after said removing optically active threo-3-amino-1,2-disulfonate derivative is further washed with water to remove the diol compound represented by the formula(1).

26. A process for purifying an optically active threo-3-amino-1,2-epoxy compound according to term 24 or 25, wherein said epoxy compound is obtained as a depositing crystalline by adjusting the temperature of the water-washed solution to −30 to 35° C.

27. A process according to term 24, wherein said aliphatic hydrocarbon type of solvent is a C5–C10 hydrocarbon.

28. A process according to term 24, wherein said aliphatic hydrocarbon type of solvent is n-heptane.

29. A process according to term 24, wherein the epoxydation of the compound of the formula(2) is carried out under the presence of an alkali metal alcoholate.

30. A process for producing an optically active threo-3-amino-1,2-epoxy compound represented by the formula (3),

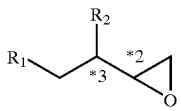
(3)

(where $R_1$ is a C3–C12 hydrocarbon residual group; $R_2$ is an amino group or a protected amino group; *2 is, if *3 is S in configuration, R in configuration and, if *3 is R in configuration, S in configuration),
which comprises reacting the optically active threo-3-amino-1,2-diol derivative represented by the formula (1)

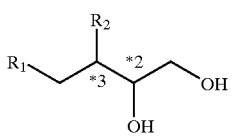
(1)

(where $R_1$, $R_2$, *2 and *3 show the same meanings as described above)
with an alkylsulfonyl halogenide for sulfonylating under the presence of a base in an organic solvent to obtain site-specifically the optically active threo-3-amino-2-hydroxy-1-alkylsulfonate derivative represented by the formula(2)

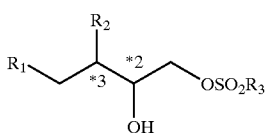
(2)

(where $R_1$, $R_2$, *2 and *3 show the same meaning as described above, and $R_3$ is a C1–C12 hydrocarbon residual group)
and then epoxydating.

31. A process for producing an optically active threo-3-amino-1,2-epoxy compound according to term 30, wherein said optically active threo-3-amino-1,2-diol derivative represented by the formula(1) is a compound obtained by reducing an optically active threo-3-amino-2-hydroxy-1-carboxylic acid alkyl ester.

32. A highly pure N-protected-3(S)-amino-1,2(R)-epoxy-4-phenyl butane or said salt obtained by the process for purifying according to any of term 24–29, wherein said N-protected-3(S)-amino-1,2(R)-epoxy-4-phenyl butane or said salt has a purity of 97% or more according to the HPLC area ratio, with the optically active threo-3-amino-1,2-disulfonate derivative as a by-product contained in a concentration of 0.5% or less according to the HPLC area ratio.

33. A Highly pure N-protected-3(s)-amino-1,2(R)-epoxy-4-phenyl butane or said salt obtained by the process for purifying according to any of term 24–29, wherein said N-protected-3(S)-amino-1,2(R)-epoxy-4-phenyl butane or said salt has a purity of 97% or more according to the HPLC area ratio, with the N-protected-3-amino-1,2-dihydroxy-4-phenyl butane derivative contained in a concentration of 0.5% or less according to the HPLC area ratio.

BEST MODE FOR CARRYING OUT THE INVENTION $R_1$ in the formula(1)–(3) of the present invention is a C3–C12, preferably C3–C8 hydrocarbon group, which may be saturated, unsaturated, straight chained, cyclic, or a their combination. It includes an alkyl group, an aryl group and an aralkyl group. These may have substituents free from the reaction. The alkyl group is preferably a C3–C8 group and includes n-propyl, isopropyl, n-butyl, isobutyl, sec-butyl, tert-butyl, pentyl, and hexyl group. A cycloalkyl group includes cyclopropyl, cyclobutyl, cyclopentyl, and cyclohexyl group. The aryl group includes an aryl group having 6 to 10 carbons in aryl structure, for example, an optionally substituted phenyl or naphthyl group including an unsubstituted phenyl group, a lower alkyl substituted phenyl group such as p-tolyl, a lower alkoxy substituted phenyl group such as 4-methoxy phenyl, a halogen substituted phenyl group such as 4-chloro phenyl, 1-naphthyl group and 2-naphthyl group. Herein, the word "lower" means C1–C8, preferably C1–C4 and hereinafter the same. The aralkyl group includes the above lower alkyl group whose hydrogen (s) is substituted with the above aryl group, and is preferably trityl group and benzyl group.

$R_2$ as a protected amino group in the formula (1)-(3) is not particularly limited. The protecting group includes (1) an acyl group, for example, a substituted or unsubstituted lower alkanoyl group such as formyl group, acetyl group, propionyl group, trifluoroacetyl group and benzoyl group, and phthaloyl group, (2) an urethane-forming protecting group, for example, a substituted or unsubstituted lower alkoxy carbonyl group such as tert-butoxy carbonyl group and tert-amyloxy carbonyl group, and an substituted or unsubstituted aralkyloxy carbonyl group such as p-nitrobenzyloxy carbonyl group and benzyloxy carbonyl group, (3) an substituted or unsubstituted arylsulfonyl group such as tosyl group and benzene sulfonyl group, (4) an aralkyl group such as trityl group and benzyl group. A substituent in the substituted lower alkanoyl group, the substituted lower alkoxy carbonyl group and the substituted aralkyloxy carbonyl group includes trifluoromethyl group, nitro group, a halogen atom and hydroxyl group. A substituent in the substituted arylsulfonyl group includes a C1–C4 lower alkyl group, trifluoromethyl group, nitro group, halogen atom and hydroxyl group.

The most popular protecting group is (1) an acyl group or (2) an urethane-forming protecting group; preferable are an substituted or unsubstituted lower alkanoyl group, an substituted or unsubstituted lower alkoxy carbonyl group and an substituted or unsubstituted aralkyloxy carbonyl group; and more preferable are tert-butoxy carbonyl group and benzyloxy carbonyl group.

A C1–C12 hydrocarbon residue represented by $R_3$ in the formula (2) is preferably a C1–C8 lower alkyl group and more preferably a C1–C4 lower alkyl group such as methyl group, ethyl group, propyl group and butyl group or an aryl group. The aryl group includes the same groups as described in the above $R_1$. Preferable is a lower alkyl substituted phenyl group.

The process of the present invention will be described in more details below.

The diol derivative represented by the formula (1) can be produced by the similar method disclosed by JP Laid-Open No.179405/1995 and JP Laid-Open No.215955/1995. An optically active threo-3-amino-2-hydroxy ester derivative generally dissolved in a solvent may be reacted with an appropriate reducing agent to obtain. The solvent is not particularly limited as long as it can dissolve the optically active threo-3-amino-2-hydroxy ester derivative, including preferably polar solvents such as alcohols and ethers. For the reducing agent, a boron type or an aluminium type such as a borohydride compound, an aluminiumhydride compound and diboran may be used. Preferable are an alkali metal borohydride and an alkaline earth metal borohydride such as sodium borohydride, lithium borohydride, calcium borohydride and zinc borohydride.

The reducing agent may be used in the 1–10, preferably 2–5 equivalent amounts relative to the reaction substrate. It may be added in any state of a solid and a solution. It may be prepared in the reaction system for the reaction to react if it is difficult to obtain on the market.

The reaction using sodium borohydride may be carried out in a lower alcohol as a rection solvent, such as methanol, ethanol and isopropanol, tetrahydrofurane, or a mixture thereof at a temperature of –20° C. to reflux temperature(for example, about 80° C.), preferably 0–50° C.

The optically active threo-3-amino-1,2-epoxy compound represented by the formula (3) can be produced by reacting the optically active threo-3-amino-1,2-diol derivative represented by the formula (1) with an alkylsulfonyl halogenide or an arylsulfonyl halogenide under the presence of a base in an organic solvent for sulfonylating, and then washing the obtained optically active threo-3-amino-2-hydroxysulfonate derivative solution with water, and thereafter epoxydating by adding a base to the separated organic phase.

The preferable organic solvent is an ether type of solvent, an ester type of solvent, an aromatic hydrocarbon type of solvent or a halogenide type of solvent. The preferable ether type of solvent is concretely a lower alkyl (C1–C5) ether such as diethyl ether, tetrahydrofurane, tert-butylmethyl ether, and particularly preferable is tetrahydrofurane. The ester type of solvent includes a lower alkyl ester (C1–C4 acyl group, C1–C4 alkoxy group) such as methyl acetate, ethyl acetate, propyl acetate, butyl acetate, methyl propionate, ethyl propionate, methyl butyrate and ethyl butyrate, and particularly preferable is ethyl acetate. The aromatic hydrocarbon type of solvent includes a benzene type of solvent (for example, unsubstituted benzene or a C1–C6 lower alkyl or halogen substituted benzene)such as toluene, xylene and benzene, and particularly preferable is toluene. The halogenide type of solvent includes 1,2-dichloroethane, methylene chloride and chloroform, and particularly preferable is methylene chloride. The most preferable organic solvent is tetrahydrofurane.

The base used for sulfonylating includes a tertiary organic amine such as triethylamine, tributylamine, pyridine and N-methylmorphorine, or an inorganic base such as an alkali metal hydroxide for example sodium hydroxide, potassium hydroxide and lithium hydroxide, and preferable is triethylamine. It may be generally used in the 0.9–3, preferably 1–1.5 equivalent amounts relative to the diol derivative represented by the formula(1). The alkylsulfonyl halogenide or the arylsulfonyl halogenide used includes a lower alkyl (preferably, C1–C3) sulfonyl halogenide such as methane sulfonyl chloride, or a benzene sulfonyl chloride substituted with a lower alkyl group, nitro group or halogen such as p-toluene sulfonyl chloride, p-nitrobenzene sulfonyl chloride and p-bromobenzene sulfonyl chloride. The alkylsulfonyl halogenide is preferable due to the stability. Methane sulfonyl chloride is particularly preferable in the present invention. It may be generally used in the 0.9–3, preferably 1–1.5 equivalent amount relative to the diol derivative represented by the formula(1) and the reaction carried out at a temperature of −20° C. to reflux temperature (for example, about 80° C.), preferably 0–60° C.

The reaction time is generally for about 0.5–1 hr. The reaction is terminated when almost the raw material is consumed.

As a post treatment after the sulfonylating reaction, the reaction solution is washed with an aqueous basic solution or an aqueous neutral salt solution such as a sodium chloride solution. The aqueous basic solution includes the aqueous solution of a basic inorganic compound, for example, the aqueous basic solution of an alkali metal compound such as an alkali metal hydroxide, an alkali metal bicarbonate and an alkali metal carbonate. The aqueous basic solutions are, for example, an aqueous sodium hydroxide solution, an aqueous potassium hydroxide solution, an aqueous lithium hydroxide solution, an aqueous sodium bicarbonate solution, an aqueous potassium bicarbonate solution, an aqueous sodium carbonate solution, an aqueous potassium carbonate solution and an aqueous ammonia solution. Preferably, the reaction solution may be washed with an aqueous sodium bicarbonate solution and then washed with an aqueous sodium chloride solution. The separated organic phase, as it is, brought to the epoxydating process.

The base used for epoxydating includes an alkali metal compound or an alkaline earth metal compound. An alkali metal alcoholate such as potassium tert-butyrte, sodium methylate, sodium ethylate and potassium ethylate, an alkali metal hydride such as sodium hydride and potassium hydride, an alkali metal hydroxide such as lithium hydroxide, sodium hydroxide and potassium hydroxide or an alkali metal carbonate such as potassium carbonate and sodium carbonate is preferable to use. An alkali metal alcoholate such as sodium methylate, sodium ethylate and potassium ethylate, which is readily dissolved in an organic solvent and promotes the reaction to make rapid progress, is more preferable.

The base may be generally used in the 1–10, preferably 1–3 equivalent amounts relative to the reaction substrate(the compound of the formula(2)) and the reaction is preferably carried out at a temperature of −20° C. to 60° C., preferably −10° C. to 10° C.

The reaction solution obtained after epoxydating is neutralized with a dilute mineral acid such as dilute hydrochloric acid and dilute sulfuric acid or an aqueous carboxylic acid solution such as citric acid and acetic acid and removed the water layer to separate the organic layer, and the solvent is distilled away to obtain a crude product of the optically active threo-3-amino-1,2-epoxy compound.

As described above, the sulfonylated derivative is preferably used without isolating it from the organic phase for the epoxydating process. However, the optically active threo-3-amino-2-hydroxysulfonate derivative may be in some cases deposited from the organic phase of the reaction system to separate the crystal and then epoxydated. In the crystal-depositing method, when the optically active threo-3-amino-1,2-diol derivative represented by the formula(1) is reacted with the alkyl sulfonyl halogenide or the aryl sulfonyl halogenide under the presence of the base in the organic solvent, it is preferably to sulfonylate it under the conditon of preventing sulfonylation of it's secondary hydroxyl group (the formation of the disulfonate) by depositing the sulfonate derivative of which the primary hydroxyl group is site-specifically sulfonylated. More preferably, to the reaction solution is added an undissolvable solvent of the object compound such as an aliphatic hydrocarbon type of solvent to increase the efficient deposition of the optically active threo-3-amino-2-hydroxysulfonate derivative represented by the formula(2).

The preferable organic solvent is the mixed solvent of an ester type of solvent with an ether type of solvent, the mixed solvent of an ester type of solvent with an aliphatic hydrocarbon type of solvent, the mixed solvent of an aromatic hydrocarbon type of solvent with an ether type of solvent, or the mixed solvent of an aromatic hydrocarbon type of solvent with an aliphatic hydrocarbon type of solvent. The preferable ester type of solvent includes a lower alkyl (C1–C4 acyl group, C1–C4 alkoxy group) ester such as methyl acetate, ethyl acetate, propyl acetate, butyl acetate, methyl propionate, ethyl propionate, methyl butyrate, ethyl butyrate, and particularly preferable is ethyl acetate. The preferable ether type of solvent includes a lower alkyl (C1–C4) ether such as isopropyl ether, diethyl ether and tert-butylmethyl ether, and particularly preferable is isopropyl ether. The aliphatic hydrocarbon type of solvent includes a C5–C10 aliphatic hydrocarbon type of solvent such as n-hexane, n-heptane and n-octane, and particularly preferable is n-heptane. The aromatic hydrocarbon type of solvent includes a benzene type of solvent (for example, unsubstituted benzene or a C1–C6 lower alkyl or halogen substituted benzene) such as toluene, xylene and benzene, and particularly preferable is toluene. The most preferable mixed solvent is a mixture of ethyl acetate and isopropyl ether.

A volume ratio in the mixed solvent is 0.1–6 volume, preferably, 1–2 volume of the ether type of solvent or the aliphatic hydrocarbon type of solvent to 1 volume of the ester type of solvent or aromatic hydrocarbon type of solvent. The mixed solvent is used in 1–10 volume(L)/mol of the diol derivative.

The base used for sulfonylating is the same as described above and preferably triethyl amine. The base is generally used in the 0.9–3, preferably 1–1.5 equivalent amounts relative to the diol derivative represented by the formula(1). The alkyl sulfonyl halogenide or the aryl sulfonyl halogenide used is the same as described above; and preferable is methane sulfonyl chloride. It is generally used in the 0.9–3, preferably 1–1.5 equivalent amounts relative to the diol derivative represented by the formula(1) and the reaction may be carried out at a temperature of −20° C. to reflux temperature(for example, about 80° C.), preferably 0–60° C.

As a post treatment after the reaction, crystals deposited in the reaction solution, as it is, is filtered to obtain mixed crystals of a large amount of the optically active threo-3-amino-2-hydroxy sulfonate derivative, an amine hydrochloride and a small amount of the optically active threo-3-amino-1,2-disulfonate derivative. The mixed crystals contain additionally an unreacted diol derivative as a part thereof and a very small amount of the optically active threo-3-amino-1-hydroxy-2-sulfonate derivative.

Further, an ether type of solvent or an aliphatic hydrocarbon type of solvent is added to the reaction solution to increase crystals deposition and then the reaction solution is filtered to obtain the mixed crystal similarly. The ether type of solvent includes a lower alkyl (C1–C4) ether such as isopropyl ether, diethyl ether and tert-butylmethyl ether, and particularly preferable is isopropyl ether. The aliphatic hydrocarbon type of solvent includes a C5–C10 aliphatic hydrocarbon type of solvent such as n-hexane, n-heptane and n-octane, and particularly preferable is n-heptane.

The sulfonylation in the crystal-depositing method can be carried out in a single solvent, for example, in an ester type of solvent, in an ether type of solvent, in an aromatic hydrocarbon type of solvent or in an aliphatic hydrocarbon type of solvent, preferably in an ester type of solvent or in an ether type of solvent, more preferably in ethyl acetate or in tetrahydrofurane, and after completion of the reaction, the reaction solution is washed with water to remove the amine hydrochloride, and then an aliphatic hydrocarbon type of solvent is added to the organic phase separated to deposit the crystals so as to obtain mixed crystals free from the amine hydrochloride. The aliphatic hydrocarbon type of solvent is the same as described above, and n-heptane is preferable.

The optically active threo-3-amino-2-hydroxy sulfonate derivative obtained as crystals can be epoxydated, for example, by adding the mixed crystals in an organic solvent and, if the amine hydrochloride is contained, washing with water to remove it, and then condensing under the presence of the base for a ring closure. The organic solvent, in which the optically active threo-3-amino-2-hydroxy sulfonate derivative can be dissolved, includes an ester type of solvent, an ether type of solvent, an aromatic hydrocarbon type of solvent and a halogenide type of solvent. The preferable ester type of solvent concretely includes a lower alkyl(C1–C4 acyl group, C1–C4 alkoxy group) ester such as methyl acetate, ethyl acetate, propyl acetate, butyl acetate, methyl propionate, ethyl propionate, methyl butyrate, ethyl butyrate; and particularly preferable is ethyl acetate. The preferable ether type of solvent includes a lower alkyl (C1–C5) ether such as diethyl ether, tetrahydrofurane and tert-butylmethyl ether, and particularly preferable is tetrahydrofurane. The aromatic hydrocarbon type of solvent includes a benzene type of solvent (for example, unsubstituted benzene or a C1–C6 lower alkyl or halogen substituted benzene)such as toluene, xylene and benzene, and particularly preferable is toluene. The halogenide type of solvent includes 1,2-dichloroethane, methylene chloride and chloroform, and particularly preferable is methylene chloride. The above mixed crystals are added into the organic solvent, washed with water and then washed with an aqueous basic solution, for example, with an aqueous basic inorganic compound solution such as an aqueous sodium hydroxide solution, an aqueous potassium hydroxide solution, an aqueous lithium hydroxide solution, an aqueous sodium bicarbonate solution, an aqueous potassium bicarbonate solution, an aqueous sodium carbonate solution, an aqueous potassium carbonate solution and an aqueous ammonia solution, preferably with an aqueous sodium bicarbonate solution to separate an organic phase, to which the base is added to condense for a ring closure(epoxydating).

The base used for epoxydating is the same as described above. An alkali metal alcoholate such as sodium methylate, sodium ethylate and potassium ethylate, which is readily dissolved in an organic solvent and promotes the reaction to make rapid progress, is preferable. The base is generally used in the 1–10, preferably 1–3 equivalent amounts relative to the reaction substrate(the compound of the formula(2)) and the reaction is carried out at a temperature of −20° C. to 60° C., preferably −10° C. to 10° C. The reaction solution obtained after epoxydating can be treated in the same way as described above to obtain a crude product of the optically active threo-3-amino-1,2-epoxy compound.

A highly pure optically active threo-3-amino-1,2-epoxy compound can be obtained by adding the crude product in an aliphatic hydrocarbon type of solvent, filtering to remove the crystal impurities, and washing if necessary.

Concretely, as the crude product of the optically active threo-3-amino-1,2-epoxy compound, which is obtained by sulfonylating the compound of the formula(1) and epoxydating the compound of the formula(2) under the presence of the base, contains the threo-3-amino-1,2-disulfonate derivative as a by-product, it is purified to remove the said by-product by way of utilizing a difference in solubility. For example, when the crude product is added in an aliphatic hydrocarbon type of solvent, the epoxy compound is dissolved but the disulfonate derivative deposits as crystals. Therefore, the disulfonate derivative can be removed from reaction system by filtration easely. The aliphatic hydrocarbon type of solvent includes a C5–C10 aliphatic hydrocarbon type of solvent such as n-hexane, n-heptane and n-octane, and particularly preferable is n-heptane. The solvent may be used in 3–30 times, preferably 5–15 times the volume of the epoxy compound(the compound of the formula(3)), though not particularly limited, and the reaction is carried out at a temperature of 0° C. to 80° C., preferably 15° C. to 50° C.

Next, preferably, the solution, in which the threo-3-amino-1,2-disulfonate derivative is removed, may be washed with water to remove the remaining threo-3-amino-1,2-diol derivative as well as the other water-soluble by-products existing in the organic solvent. The waterwashing is preferably repeated several times.

The extraction solution is condensed to isolate a highly pure optically active threo-3-amino-1,2-epoxy compound, which can be obtained either as an oily product under heating at a temperature of about 40° C. or higher as a crystalline product by cooling. It is preferably isolated as a crystalline product because of the easy handling.

The crystallization of the active threo-3-amino-1,2-epoxy compound is carried out by gradually cooling the extraction solution, as it is or condensed a little, preferably to −30 to −5° C.

The epoxy compound thus obtained has a high purity, which is attainable by no conventional process, of 97% or more, or 98% or more according to the HPLC area ratio and respective content of the threo-3-amino-1,2-disulfonate derivative as the by-product and the diol compound as the remaining raw material in the epoxy compound is 0.5% or less according to the HPLC area ratio. Therefore, this epoxy compound is suitable for a material for drug.

The formula(1)compound in the present invention includes the following compounds:

[1] N-tert-butoxycarbonyl-3(S)-amino-2(R)-hydroxy-4-phenyl-1-butanol;
[2] N-tert-butoxycarbonyl-3(R)-amino-2(S)-hydroxy-4-phenyl-1-butanol;
[3] N-benzyloxycarbonyl-3(S)-amino-2(R)-hydroxy-4-phenyl-1-butanol;
[4] N-benzyloxycarbonyl-3(R)-amino-2(S)-hydroxy-4-phenyl-1-butanol;
[5] N-benzoyl-3(S)-amino-2(R)-hydroxy-4-phenyl-1-butanol;
[6] N-benzoyl-3(R)-amino-2(S)-hydroxy-4-phenyl-1-butanol.

The formula(2)compound in the present invention includes the following compounds:

[1] N-tert-butoxycarbonyl-3(S)-amino-2(R)-hydroxy-4-phenyl-1-methane sulfonyloxybutane;
[2] N-tert-butoxycarbonyl-3(R)-amino-2(S)-hydroxy-4-phenyl-1-methane sulfonyloxybutane;
[3] N-benzyloxycarbonyl-3(S)-amino-2(R)-hydroxy-4-phenyl-1-methane sulfonyloxybutane;
[4] N-benzyloxycarbonyl-3(R)-amino-2(S)-hydroxy-4-phenyl-1-methane sulfonyloxybutane;

[5] N-benzoyl-3(S)-amino-2(R)-hydroxy-4-phenyl-1-methane sulfonyloxybutane;
[6] N-benzoyl-3(R)-amino-2(S)-hydroxy-4-phenyl-1-methane sulfonyloxybutane.

The formula(3)compound in the present invention includes the following compounds:

[1] N-tert-butoxycarbonyl-3(S)-amino-1,2(R)-eoxy-4-phenyl butane;
[2] N-tert-butoxycarbonyl-3(R)-amino-1,2(S)-eoxy-4-phenyl butane;
[3] N-benzyloxycarbonyl-3(S)-amino-1,2(R)-eoxy-4-phenyl butane;
[4] N-benzyloxycarbonyl-3(R)-amino-1,2(S)-eoxy-4-phenyl butane;
[5] N-benzoyl-3(S)-amino-1,2(R)-eoxy-4-phenylbutane;
[6] N-benzoyl-3(R)-amino-1,2(S)-eoxy-4-phenylbutane.

EXAMPLE

The present invention will be described in more details with reference to Reference Examples and Examples as shown below, but shall not be limited to these examples.

Reference Example 1

N-tert-butoxycarbonyl-3(S)-amino-2(R)-hydroxy-4-phenyl-1-butanol

A solution of N-tert-butoxycarbonyl-3(S)-amino-2(R)-hydroxy-4-phenylbutyric acid methyl ester 99 g dissolved in ethanol 130 ml was kept at 15–25° C. and mixed with sodium borohydride 15.7 g and stirred at 15–25° C. for 2.5 hrs. The reaction solution was diluted with water, adjusted with 6N-HCl to pH 2.5–3.5 and thereafter the solvent was distilled away to half the volume of the resultant solution, and then ethyl acetate was added to the solution. The solution thus obtained was washed with water and aqueous 10% sodium chloride solution successively to separate an organic phase. The solvent in the organic phase was distilled away and then ethyl acetate was added to the resultant concentrated solution to cool it and n-heptane was added to the solution halfway. Further n-heptane was added to the cloudy solution obtained. Thereafter, the solution was stirred at 10° C. to deposit crystals, which were filtered and dried in vacuum to obtain the N-tert-butoxycarbonyl-3(S)-amino-2(R)-hydroxy-4-phenyl-1-butanol(65.4 g).

[α] 20D=−33.2° (C=1.0, methanol) 200 MHz 1H NMR (CDCl3) δ; 1.40 (s, 9H), 2.59 (d, 1H), 2.91 (d, 2H), 3.02 (t, 1H), 3.40–3.73 (m, 3H), 3.92 (m, 1H), 4.85 (d, 1H), 7.16–7.38 (m, 5H) mp 95–96° C.

Reference Example 2

N-tert-butoxycarbonyl-3(S)-amino-2(R)-hydroxy-4-phenyl-1-butanol

A solution of N-tert-butoxycarbonyl-3(S)-amino-2(R)-hydroxy-4-phenylbutyric acid methyl ester 154.7 g dissolved in ethanol 300 ml was kept at 5–15° C. and mixed with sodium borohydride 24.6 g and stirred at 15–45° C. for 3 hrs. The reaction solution was cooled and adjusted with 3N-HCl to pH 2.5–3.5. Water was added to the resultant solution and then the obtained solution was cooled to 5° C. or lower to deposit crystals. The crystals were filtered, dissolved in ethyl acetate, and washed with aqueous 5% sodium bicarbonate solution to separate an organic phase, which was washed with aqueous 10% sodium chloride solution and concentrated under an reduced pressure to obtain the crude N-tert-butoxycarbonyl-3(S)-amino-2(R)-hydroxy-4-phenyl-1-butanol.

Reference Example 3

N-tert-butoxycarbonyl-3(S)-amino-2(R)-hydroxy-4-phenyl-1-butanol

A solution of N-tert-butoxycarbonyl-3(S)-amino-2(R)-hydroxy-4-phenylbutyric acid methyl ester 85.1 kg dissolved in ethanol 220 kg was kept at 10–20° C. and mixed with sodium borohydride 13.5 kg and stirred at 15–45° C. for 3 hrs. The reaction solution was cooled, adjusted with 3N-HCl to pH 2.5–3.5, concentrated under a reduced pressure, and washed with ethyl acetate and water to separate an organic phase, which was washed with aqueous 10% sodium chloride solution and concentrated under an reduced pressure to obtain the crude N-tert-butoxycarbonyl-3(S)-amino-2(R)-hydroxy-4-phenyl-1-butanol.

Example 1

N-tert-butoxycarbonyl-3(S)-amino-2(R)-hydroxy-4-phenyl-1-methane sulfonyloxybutane To a solution of N-tert-butoxycarbonyl-3(S)-amino-2(R)-hydroxy-4-phenyl-1-butanol 65.42 g(Net.63.38 g)dissolved in ethyl acetate 320 ml were added isopropyleter 320 ml, and then methane sulfonylchloride 28.3 g under ice-cooling, and triethylamine 25.0 g, successively, and the solution was stirred for 1 hr. N-heptane was added to the reaction solution and the solution was stirred for further 1 hr to deposit crystals, which were filtered and dried in vacuum to obtain the crude N-tert-butoxycarbonyl-3(S)-amino-2(R)-hydroxy-4-phenyl-1-methane sulfonyloxybutane 89.3 g (Net.55.7 g). The crude crystals. A ratio of main components in the crude crystals, which contain triethylamine hydrochloride, is the diol derivative compound: the 2-sulfonate derivative: the 1-sulfonate derivtive(the object product): the 1,2-disulfonate compound=1.3:0.1:95.4:3.2. A part of the crude crystal was dissolved in ethyl acetate, washed with water, and purified by recrystallization from ethyl acetate and isopropyl ether. The purified recrystals were used for anlysyses.

[α] 20D=−33.9° (C=1.0, methanol) 200 MHz 1H NMR (CDCl3) δ; 1.41 (s, 9H), 2.54 (b, 1H), 2.95 (m, 2H), 3.02 (s, 3H), 3.80 (m, 1H), 3.89 (m, 1H), 4.12–4.30 (m, 2H), 4.90 (d, 1H), 7.17–7.38 (m, 5H) mp 102–108° C.

Example 2

N-tert-butoxycarbonyl-3(S)-amino-2(R)-hydroxy-4-phenyl-1-methane sulfonyloxybutane To a solution of the crude N-tert-butoxycarbonyl-3(S)-amino-2(R)-hydroxy-4-phenyl-1-butanol obtained in Reference Example 3 and dissolved in ethyl acetate 250 kg were added isopropylether 230 kg, methane sulfonylchloride 34.7 kg at 20–30° C., and triethylamine 30.6 kg and stirring at 30-40° C. for 1 hr. N-heptane was added to the reaction solution and the obtained solution was cooled down to 5° C. or lower to deposit crystals, which were filtered by centrifugation to obtain a wet crystal of crude N-tert-butoxycarbonyl-3(S)-amino-2(R)-hydroxy-4-phenyl-1-methane sulfonyloxybutane 153.6 kg (Net.60.6 kg).

Example 3

N-tert-butoxycarbonyl-3(S)-amino-2(R)-hydroxy-4-phenyl-1-methane sulfonyloxybutane N-tert-butoxycarbonyl-3(S)-amino-2(R)-hydroxy-4-phenyl-butyric acid methyl ester 340.4 kg was reduced with sodium borohydride by the same way as described in Reference Example 3, to obtain the crude N-tert-butoxycarbonyl-3(S)-amino-2(R)-hydroxy-4-phenyl-1-butanol, which was dissolved in ethyl acetate 988 kg. To the solution were added methane sulfonylchloride 130.7 kg at 15–0° C. and triethylamine 115.4 kg, successively, and the solution was stirred at 20–30° C. for 15 min. The reaction solution was washed with aqueous 5% sodium bicarbonate solution to separate an organic phase, which was washed with aqueous 10% sodium chloride solution. The separated organic phase was mixed with n-heptane and cooled gradually down to 5° C. or lower to deposit crystals, which were filtered by a Nutsche funnel to obtain a wet crystal of crude N-tert-butoxycarbonyl-3(S)-amino-2(R)-hydroxy-4-phenyl-1-methanesulfonyloxybutane 793 kg (Net.368.9 kg).

Example 4

N-tert-butoxycarbonyl-3(S)-amino-1,2(R)-epoxy-4-phenyl Butane

To a solution of N-tert-butoxycarbonyl-3(S)-hydroxy-4-phenyl-1-methanesulfonyloxybutane(the 2-hydroxy-1-sulfonate compound: the 1-hydroxy-2-sulfonate compound: the diol compound: the 1,2-disulfonate compund=97.1:0.1:0.4:2.3 according to the HPLC area ratio) 50 g dissolved in ethyl acetate 510 ml was added 28% sodium methylate methanol solution 58.2 g under ice-cooling and stirred for 10 min. The reaction solution was diluted with water and adjusted with 6N-HCl to pH7 to separate an organic phase, which was distilled to remove the solvent. The concentrated residue was mixed with n-heptane, stirred at the ambient temperature for 1 hr to deposit crystals, which were filtered to remove. The filtrate was washed with water to separate an organic phase, which was mixed with active charcoal 2 g, stirred at the ambient temperature for 1 hr and filtered to remove charcoal. The filtrate was cooled down to −20° C. to deposit crystals, which were filtered and dried in vacuum to obtain the N-tert-butoxycarbonyl-3(S)-amino-1,2(R)-epoxy-4-phenylbutane(98.5% according to the HPLC area ratio) 28.8 g. The diol compound and the 1,2-disulfonate compound contained in a concentration of 0.5% or less in the crystals according to the HPLC area ratio respectively.

[α] 20D=−15.9° (C=1.0, methanol) 200 MHz 1H NMR (CDCl3) δ; 1.40 (s, 9H), 2.58 (m, 1H), 2.69 (t, 1H), 2.81–3.05 (m, 3H), 4.12 (m, 1H), 4.49 (m, 1H), 7.17–7.38 (m, 5H) mp 46–47° C.

Example 5

N-tert-butoxycarbonyl-3(S)-amino-1,2(R)-epoxy-4-phenyl Butane

To a solution of the crude N-tert-butoxycarbonyl-3(S)-amino-2(R)-hydroxy-4-phenyl-1-Butanol obtained in Reference Example 2 and dissolved in tetrahydrofurane 750 ml were added methane sulfonylchoride 63.25 g at 15–20 ° C. and then triethylamine 55.83 g and the solution was stirred at 15–25° C. for 1 hr. The reaction solution was washed with an aqueous 5% sodium bicarbonate solution to separate an organic phase, which was washed with an aqueous 10% sodium chloride solution. To the separated organic phase was added a 28% sodium methylate methanol solution 96.5 g at −5° C. to 5° C. and stirred at 0° C. to 10° C. for 30 min. The reaction solution was diluted with water and adjusted with 6N-HCl to pH6.5–7.5 to separate an organic phase, which was distilled to remove the solvent. The concentrated residue was mixed with n-heptane, stirred at the ambient temperature for 1 hr to deposit crystals, which were filtered to remove. The filtrate was washed with water to separate an organic phase, which was mixed with active charcoal 1.1 g, stirred at the ambient temperature for 30 min and filtered to remove the active charcoal. The filtrate was cooled down to −20° C. to deposit crystals, which were filtered and dried in vacuum to obtain an object product, namely the N-tert-butoxycarbonyl-3(S)-amino-1,2(R)-epoxy-4-phenyl-butane (98.6% according to the HPLC area ratio)99.46 g. The diol compound and the 1,2-disulfonate compound contained in a concentration of 0.5% or less in the object product according to the HPLC area ratio respectively. 12.3 g of the object product was lost into the filtered liquid.

Example 6

N-tert-butoxycarbonyl-3(S)-amino-1,2(R)-epoxy-4-phenyl-butane

The wet crystal of crude N-tert-butoxycarbonyl-3(S)-amino-2(R)-hydroxy-4-phenyl-1-methanesulfonyloxybutane 153.6 kg obtained in Example 2 was dissolved in ethyl acetate 370 kg, washed with water and then washed with an aqueous 5% sodium bicarbonate solution. To the obtained organic phase were a 28% sodium methylate methanol solution 53.1 kg at 5° C. or lower and the organic phase was stirred for 30 min. The reaction solution was diluted with water and adjusted with 3N-HCl to pH6.5-7.5 to separate an organic phase, which was distilled to remove the solvent. The concentrated residue was mixed with n-heptane, stirred at 30–40° C. for 1 hr to deposit crystals, which were filtered to remove. The filtrate was washed with water to separate an organic phase, which was mixed with active charcoal 0.6 kg, stirred at the ambient temperature for 30 min and filtered to remove the active charcoal. The filtrate was distilled to remove the solvent into half the volume, mixed with n-heptane, and cooled gradually down to −20° C. to deposit crystals, which were filtered and dried in vacuum to obtain an object product, the N-tert-butoxycarbonyl-3(S)-amino-1,2(R)-epoxy-4-phenyl butane (99.8% according to the HPLC area ratio)40.1 kg. The object product 1.6 kg was lost into the filtered liquid.

Example 7

N-tert-butoxycarbonyl-3(S)-amino-1,2(R)-epoxy-4-phenyl-butane

The wet crystal of crude N-tert-butoxycarbonyl-3(S)-amino-2(R)-hydroxy-4-phenyl-1-methanesulfonyloxybutane 793 kg obtained in Example 3 was dissolved in ethyl acetate 1482 kg. To the solution were a 28% sodium methylate methanol solution 245 kg at 5° C. or lower and the solution was stirred for 30 min. The reaction solution was diluted with water and adjusted with 3N-HCl to pH6.5–7.5 to separate an organic phase, which was distilled to remove the solvent. The concentrated residue was mixed with n-heptane, stirred at 30–40° C. for 1 hr to deposit crystals, which were filtered to remove The filtrate was washed with water to separate an organic phase, which was mixed with active charcoal 2.4 kg, stirred at the ambient temperature for 30 min and filtered to remove the active charcoal. The filtrate was distilled to remove the solvent into half the volume, mixed with n-heptane, and cooled gradually down to −20° C. to deposit crystals, which were filtered and dried in vacuum to obtain an object product, the N-tert-butoxycarbonyl-3(S)-amino-1,2(R)-epoxy-4-phenylbutane (99.6% according to the HPLC area ratio) 200.7 kg. The object product 10.2 kg were lost into the filtered liquid.

Industrial Applicability

The present invention can, in an industrial scale, produce a highly pure optically active threo-3-amino-1,2-epoxy compound suitable for a material for drug.

What is claimed is:

1. A process for purifying an optically active threo-3-amino-1,2-epoxy compound represented by the formula (3),

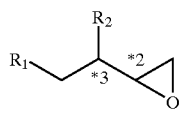

(3)

(where $R_1$ is a C3–C12 hydrocarbon residual group; $R_2$ is an amino group or a protected amino group; *2 is, if *3 is S in configuration, R in configuration and, if *3 is R in configuration, S in configuration), which comprises reacting the optically active threo-3- amino-1,2-diol derivative represented by the formula (1)

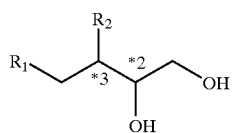

(1)

(where $R_1$, $R_2$, *2 and *3 show the same respective meanings as described above) with an alkylsulfonyl halogenide or an arylsulfonyl halogenide for sulfonylating under the presence of a base in an organic solvent to obtain site-specifically the optically active threo-3-amino-2-hydroxysulfonate derivative represented by the formula (2)

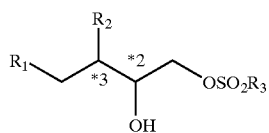

(2)

(where $R_1$, $R_2$, *2 and *3 show the same respective meanings as described above, and $R_3$ is a C1–C12 hydrocarbon residual group) and then epoxydating under the presence of a base and thereafter removing selectively a by-product, namely, optically active threo-3-amino-1,2-disulfonate derivative as a depositing crystalline by using an aliphatic hydrocarbon type of solvent and utilizing difference in solubility between the epoxy compound and the by-product.

2. A process for purifying an optically active threo-3-amino-1,2-epoxy compound according to claim 1, wherein the solution obtained after removing optically active threo-3- amino-1,2-disulfonate derivative is further washed with water to remove the diol compound represented by the formula (1).

3. A process for purifying an optically active threo-3-amino-1,2-epoxy compound according to claim 1 or 2, wherein said epoxy compound is obtained as a depositing crystalline by adjusting temperature of the water-washed solution to −30 to 35° C.

4. A process according to claim 1, wherein said aliphatic hydrocarbon type of solvent is a C5–C10 hydrocarbon.

5. A process according to claim 1, wherein said aliphatic hydrocarbon type of solvent is n-heptane.

6. A process according to claim 1, wherein epoxydation of the compound of the formula (2) is carried out under the presence of an alkali metal alcoholate.

7. A Highly pure N-protected-3(S)-amino-1,2(R)-epoxy-4- phenyl butane or said salt obtained by the process for purifying according to any of claim 1–6, wherein said N-protected- 3(S)-amino-1,2(R)-epoxy-4phenyl butane or said salt has a purity of 97% or more according to the HPLC area ratio, with the optically active threo-3-amino-1,2-disulfonate derivative as a by-product contained in a concentration of 0.5% or less according to the HPLC area ratio.

8. A Highly pure N-protected-3(S)-amino-1,2(R)-epoxy-4- phenyl butane or said salt obtained by the process for purifying according to any of claim 1–6, wherein said N-protected- 3(S)-amino-1,2(R)-epoxy-4phenyl butane or said salt has a purity of 97% or more according to the HPLC area ratio, with the N-protected-3amino-1,2-dihydroxy-4phenyl butane derivative contained in a concentration of 0.5% or less according to the HPLC area ratio.

9. A process for purifying a 3-amino-1,2-epoxy compound represented by the formula (3),

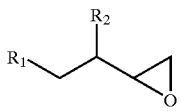

(3)

(where $R_1$ is a C3–C12 hydrocarbon residual group; $R_2$ is an amino group or a protected amino group;), which comprises reacting the 3-amino-1,2-diol derivative represented by the formula (1)

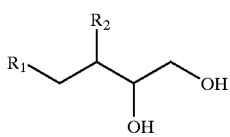

(1)

(where $R_1$ and $R_2$ show the same respective meanings as described above) with an alkylsulfonyl halogenide or an arylsulfonyl halogenide for sulfonylating under the presence of a base in an organic solvent to obtain site-specifically the 3-amino-2-hydroxysulfonate derivative represented by the formula (2)

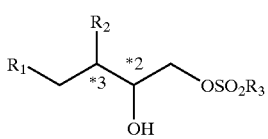

(2)

(where $R_1$ and $R_2$ show the same respective meanings as described above, and $R_3$ is a C1–C12 hydrocarbon residual group) and then epoxydating under the presence of a base and thereafter removing selectively a by-product, namely, 3-amino-1,2-disulfonate derivative as a depositing crystalline by using an aliphatic hydrocarbon type of slovent and utilizing difference in solubility between the epoxy compound and the by-product.

* * * * *